United States Patent
Olafsson et al.

(10) Patent No.: US 8,114,168 B2
(45) Date of Patent: Feb. 14, 2012

(54) MOMENTUM FREE BEARING FOR USE IN PROSTHETIC AND ORTHOTIC DEVICES

(75) Inventors: Sigurdur Olafsson, Reykjavik (IS); Gudni Ingimarsson, Reykjavik (IS); Helgi Jonsson, Reykjavik (IS)

(73) Assignee: Ossur HF, Reykjavik (IS)

(*) Notice: Subject to any disclaimer, the term of this patent is extended or adjusted under 35 U.S.C. 154(b) by 1192 days.

(21) Appl. No.: 11/896,960

(22) Filed: Sep. 7, 2007

(65) Prior Publication Data

US 2008/0071387 A1    Mar. 20, 2008

Related U.S. Application Data

(60) Provisional application No. 60/845,503, filed on Sep. 19, 2006.

(51) Int. Cl.
*A61F 2/62* (2006.01)
*F16F 9/24* (2006.01)

(52) U.S. Cl. .......................... 623/39; 188/297

(58) Field of Classification Search .............. 623/24, 623/39–45; 188/297
See application file for complete search history.

(56) References Cited

U.S. PATENT DOCUMENTS

| | | | |
|---|---|---|---|
| 42,799 A | 5/1864 | Shepard | |
| 409,311 A | 8/1889 | Snyder | |
| 3,168,014 A | 2/1965 | Aslan | |
| 3,790,965 A | 2/1974 | Gelbenegger | |
| 3,977,259 A | 8/1976 | Goldfein | |
| 5,092,902 A | 3/1992 | Adams et al. | |
| 5,376,137 A | 12/1994 | Shorter et al. | |
| 5,403,167 A | 4/1995 | Kobayashi et al. | |
| 5,405,409 A | 4/1995 | Knoth | |
| 5,443,521 A | 8/1995 | Knoth et al. | |
| 5,728,172 A | 3/1998 | Krieger | |
| 5,746,774 A * | 5/1998 | Kramer et al. | 623/39 |
| 5,888,212 A | 3/1999 | Petrofsky et al. | |
| 5,895,430 A * | 4/1999 | O'Connor | 623/39 |
| 5,989,294 A | 11/1999 | Marlow | |
| 6,113,642 A * | 9/2000 | Petrofsky et al. | 623/24 |
| 6,322,594 B1 * | 11/2001 | Boiten et al. | 623/27 |
| 6,613,097 B1 | 9/2003 | Cooper | |
| 6,752,835 B2 * | 6/2004 | Shen | 623/44 |
| 7,582,119 B2 * | 9/2009 | Chen | 623/39 |
| 2004/0181289 A1 | 9/2004 | Bedard et al. | |
| 2006/0069449 A1 * | 3/2006 | Bisbee et al. | 623/26 |
| 2006/0136072 A1 | 6/2006 | Bisbee, III et al. | |

OTHER PUBLICATIONS

Office Action dated Nov. 12, 2010 in corresponding Chinese application No. 200780034788.6 (and English language translation).

* cited by examiner

*Primary Examiner* — Thomas C. Barrett
*Assistant Examiner* — Christopher Beccia
(74) *Attorney, Agent, or Firm* — Bacon & Thomas, PLLC

(57) ABSTRACT

A momentum free bearing assembly for use in orthotic and prosthetic devices and a prosthetic knee incorporating the same are disclosed. The bearing assembly includes an engaging ring having a swivel portion received within the engaging ring. The engaging ring is received within a bore in a mount. Retainer rings may be placed on either side of the engaging ring within the bore to retain the engaging ring within the mount. Seals having sealing members may be provided on either side of the engaging ring to seal the engaging ring within the mount. A cylindrical rod engages the swivel portion and the seal through bores provided in each of the seal and the swivel portion. The ends of the cylindrical rod can be press-fit within bores on a mount and a frame of a prosthetic knee.

12 Claims, 5 Drawing Sheets

MOMENTUM FREE BEARING FOR USE IN PROSTHETIC AND ORTHOTIC DEVICES

This application claims the benefit of U.S. Provisional Application No. 60/845,503, filed Sep. 19, 2006.

FIELD OF THE INVENTION

The present invention relates generally to the field prosthetic and orthotic devices, and more particularly to a momentum free bearing assembly for use as a joint connection in prosthetic and orthotic devices.

BACKGROUND

Bearing assemblies in orthotic devices and prosthetic limbs, such as prosthetic knees, traditionally allow one degree-of-freedom of movement between joint connections. That is, the bearings allow the connections to rotate about a single axis, while limiting the movement of the connections in all other directions. Examples of prosthetic limbs using conventional single degree-of-freedom bearing assemblies are described in U.S. Pat. Nos. 5,092,902 (Adams et al.), 5,376,137 (Shorter et al.), 5,443,521 (Knoth et al.), and 5,895,430 (O'Conner) all herein incorporated by reference.

The conventional single degree-of-freedom bearing assemblies have the disadvantage of transferring torsional loads to the linkages of the joint connection. In a common prosthetic knee, torsional loading can occur during the stance phase of the gait cycle, which involves a user planting his foot. In particular, torsional loads can arise when a person using a prosthetic knee plants the foot associated with the prosthetic knee, and rotates their torso and other leg in order to accomplish a turn. During this turn the prosthetic knee will see torsional loading.

Because of the transfer of torsional loading between the linkages, the linkages must be designed to withstand the torsional forces that buildup within the linkages. This typically entails providing a linkage that has a larger diameter or cross-sectional area.

Such larger linkages can add substantially to the weight of a prosthetic device especially for example in prosthetic knees that are mechanically complex and employ a plurality of hinge or rotation points that allow variations in the action of the knee throughout the gait cycle. An example of one such prosthetic joint is disclosed in the Shorter et al. patent.

Additionally, for prosthetic limbs having a control unit such as a hydraulic cylinder, the transferred torsional loads can cause binding between the piston and cylinder. This can lead to the prosthetic limb performing in an unexpected manner and possibly damaging the piston and cylinder, which are expensive to replace.

It would thus be beneficial to provide a joint connection that eliminates or reduces the torsional loads transferred to the linkages of an orthotic or prosthetic device. Such a connection would isolate complex or expensive components from torsional loading, and subject them to axial loading only.

The present invention provides just such a connection by providing a momentum free connection between linkages, and thus effectively isolating the linkages from torsional loading, as described below.

SUMMARY

In order to provide an improved connection for an orthotic or a prosthetic limb, a momentum free bearing assembly for use as a joint connection in orthotic or prosthetic devices is described. The momentum free bearing assembly of this disclosure provides the ability for movement between linkages in three degrees-of-freedom, allowing for some rotation between the linkages about three axes, instead of just one.

Most orthotic or prosthetic devices, such as prosthetic knees, are subject to torsional loading. Use of the momentum free bearing of this disclosure in orthotic and prosthetic devices can isolate some of the more complex components of an orthotic or prosthetic device from torsional loading.

This isolation of the complex components can allow for a linkage or control unit of an orthotic or prosthetic device to be subject to an axial load only, while the less complex and easier to manufacture bearing assemblies eliminate the torsional loading from the linkage or control unit. This prevents undue stress in the complex component.

This elimination or reduction in torsional loading of a linkage provides numerous benefits. For example, a linkage can have a reduced diameter or cross-sectional area since it will not be required to carry torsional loads. A reduced diameter or cross-sectional area linkage can provide weight savings, which is very important in the field of orthotic devices and prosthetic limbs, since it is more difficult and requires more energy for a person to utilize heavier orthotics and prosthetic limbs than lighter orthotics and prosthetic limbs.

Another advantage can be realized when a prosthetic limb uses a control unit such as a hydraulic piston type control unit. These control units are well known in the art, some examples are disclosed in the Adams et al. Shorter et al. and Knoth et al. patents. The bearing assembly of this disclosure can be used with any of the currently known or any future developed control units. These control units can also be made lighter and smaller if they are not subjected to torsional loading. In addition, the elimination of torsional loading reduces the risk that a piston could bind and catch in a cylinder, thus reducing the possibility that the prosthetic limb would behave in a manner that is unexpected by the user, and reducing the risk of damage to the expensive components of the control unit.

The reduction or elimination of torsional loading of a linkage, or active or passive control unit also provides the benefit of reduced wear on the more expensive components of the orthotic device or the prosthetic limb, while shifting the loads to more durable and possibly less expensive components.

Because the bearing assemblies according to this disclosure allow for rotation about three axes, little or no torsional loads are transmitted between the components that are connected through the bearing assemblies. Instead, the frame of an orthotic device or a prosthetic joint utilizing bearing assemblies in accordance with this disclosure support most or all of the torsional loading that may arise during the use of such an orthotic device or a prosthetic limb.

The momentum free bearing assembly of the disclosure isolates the linkages of a joint connection in orthotic and prosthetic devices from torsional loading from a frame through the following structural configuration. The bearing assembly has an engaging ring for receiving a swivel portion that is configured to swivel within the engaging ring in three directions. The bearing assembly further includes a cylindrical rod that is configured to engage a bore within the swivel portion to allow the rod to rotate in three degrees-of-freedom with respect to the engaging ring. The engaging ring is configured to engage a portion of the linkage and each end of the cylindrical rod is configured to engage the frame in a fixed manner, so that the linkage is isolated from torsional loading and can rotate in three degrees-of-freedom with respect to the frame.

The linkage may have a mount that is configured to receive the engaging ring in a fixed manner within a bore inside the mount. The bearing assembly further comprises a plurality of retaining rings that are configured to be received within the bore of the mount on either side of the engaging ring in order to retain the engaging ring within the bore of the mount. The mount may include an extending portion that allows the mount to be removably connected to a linkage, or to an active or passive control unit.

The bearing assembly may include a plurality of seals. The plurality of seals of the bearing assembly are configured to engage the mount in a sealing manner in order to seal the retaining rings and the engaging ring within the mount.

The plurality of seals each may have receiving portions that are configured to receive sealing members. The sealing members can be resilient sealing members such as conventional O-rings, gaskets, or sealing compounds such as RTV silicones.

The bearing assembly can be used as a joint connection within an orthotic device or a prosthetic limb, such as a prosthetic elbow, hip, ankle or knee joint. An orthotic or prosthetic joint may comprise a frame having proximal and distal portions and a first proximal mount engaging the proximal portion of the frame in a pivotal manner. The orthotic or prosthetic joint also has a linkage having proximal and distal portions, which can be a simple mechanical linkage or a more complex active or passive control unit. The linkage has a first pivot connection between the proximal portion of the linkage and the first proximal mount and a second pivot connection between the distal portion of the linkage and a distal portion of the frame. The first and second pivot connections may include some or all of the features of the bearing assembly described above.

The first proximal mount may have a plurality of flange portions. Each of the flange portions may include a bore for receiving a cylindrical rod of a bearing assembly of the first pivotal connection in a fixed manner, such that the linkage can rotate with respect to the first proximal mount.

The frame of the orthotic or prosthetic joint may have bores at a distal portion thereof for receiving a cylindrical rod of a bearing assembly of the second pivotal connection in a fixed manner, such that the linkage rotates in three directions with respect to the frame.

The orthotic or prosthetic joint may include bores in the first proximal mount and in the distal portion of the frame for receiving cylindrical rods of bearing assemblies, such that the linkage can rotate in three directions with respect to both the first proximal mount and the frame, respectively.

The numerous advantages, features and function of the momentum free bearing assembly and a prosthetic limb incorporating the bearing assembly will become readily apparent and better understood in view of the following description, appended claims, and accompanying drawings. The following description is not intended to limit the environments in which the momentum free bearing assembly may be used, but instead merely provides exemplary embodiments for ease of understanding.

BRIEF DESCRIPTION OF THE DRAWINGS

FIG. 6 is a perspective view of a swivel portion received within an engaging portion of a bearing assembly as shown in FIG. 1.

FIG. 7 is a perspective view of a seal of a bearing assembly as shown in FIG. 1.

FIG. 8 is a perspective view of a retainer ring of a bearing assembly as shown in FIG. 1.

Figure 1:
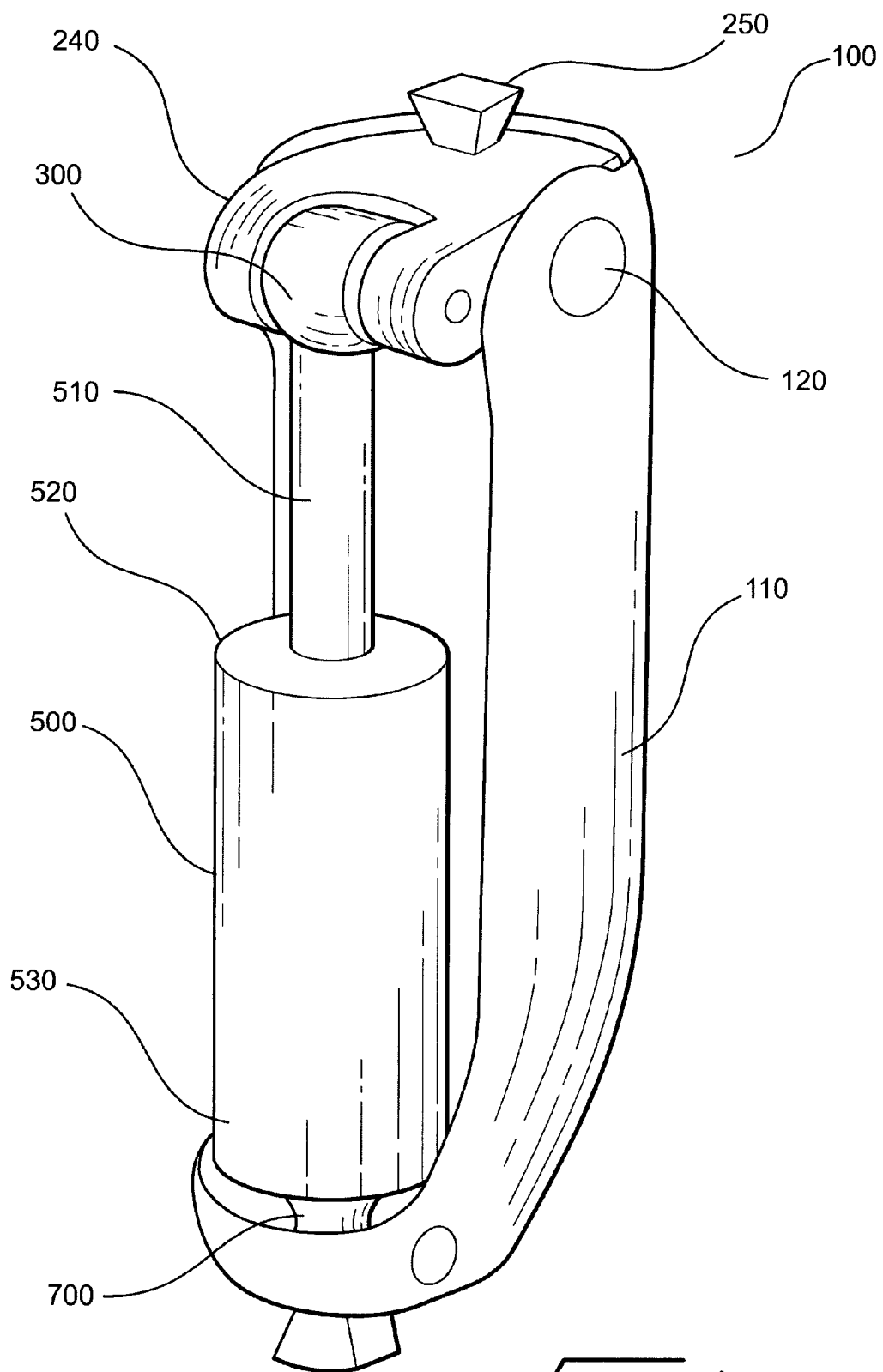
FIG. 1 is a generalized perspective view of a prosthetic knee incorporating momentum free bearing assemblies.

The features in the drawing figures are generalized and not shown to scale, so that the features thereof may be more clearly demonstrated.

DETAILED DESCRIPTION OF VARIOUS EMBODIMENTS

A. Environment and Context of the Various Embodiments

Orthotic and prosthetic devices can include mechanically simple connections allowing for a relatively simple movement of the supported body part or prosthetic device. They can also include mechanically complex hinges and connections that allow the orthotic or prosthetic device to reproduce a complex range of motions.

Due to the complexity of the motions of body parts supported by orthotic devices and prosthetic devices that reproduce the movements of body parts, these devices are typically subject to torsional loading. The momentum free bearing as disclosed can be used in any application where it is beneficial to eliminate torsional loads and to transmit an axial load only. Such environments could include orthotic devices such as hip, knee, elbow, leg, arm, back or any type of brace or other orthotic device as well as any type of prosthetic device such as prosthetic limbs, including foot, elbow and hip joints.

For further ease of understanding the momentum free bearing assembly and the use of a momentum free bearing assembly in a prosthetic knee joint as disclosed herein, a description of a few terms is necessary. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead or to the front of another location.

B. Detailed Description of a First Embodiment

The momentum free bearing assembly of this disclosure is described for use in a prosthetic knee for ease of understanding. This description is not intended to be limiting; on the contrary, the momentum free bearing assembly can be used in any appropriate orthotic or prosthetic device.

In one exemplary use, a first embodiment of a prosthetic knee including momentum free bearing assemblies is shown in FIG. 1. The prosthetic knee 100 includes a frame 110 that supports the structure of the prosthetic knee 100, as well as transmits a portion of the weight of a user's body to any type of known prosthetic foot (not shown), which may be aesthetic or utilitarian in design. The prosthetic knee joint 100 is connected to any type of known socket for receiving a residuum (not shown) at a proximal end through any conventional connection such as a pyramid connection. Some examples of conventional pyramid connections are part numbers A-135100, A-235300, A-335100, and A-435120 all available from Össur hf., Reykjavik, Iceland. As already mentioned, the prosthetic knee 100 is also connected to a prosthetic foot through any conventional connection such as a pyramid connection.

Figure 2:
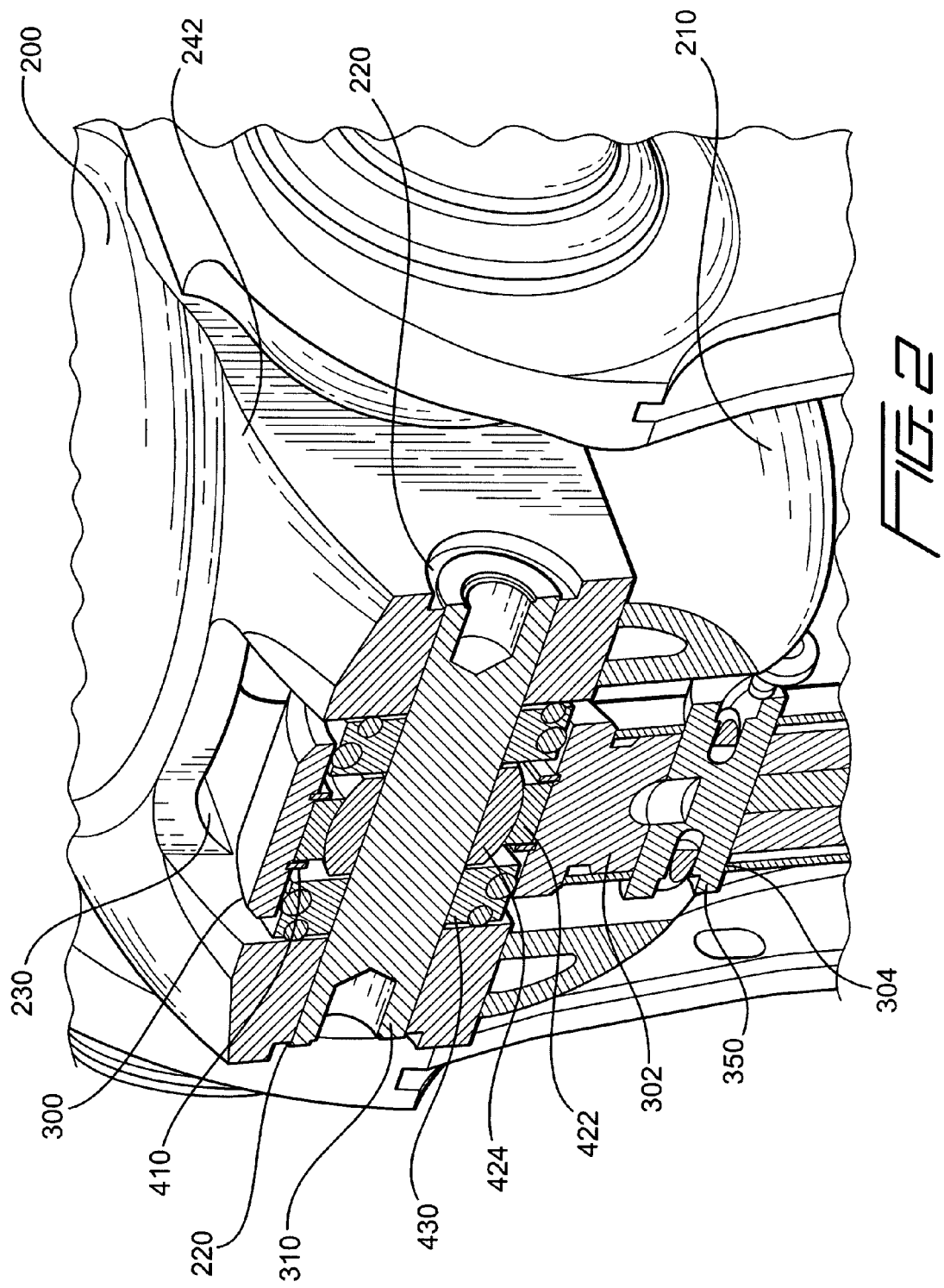
FIG. 2 is a close up sectional view of the proximal bearing assembly shown in FIG. 1.

The prosthetic knee 100 includes a proximal mount assembly 200, which can be seen in cross section in FIG. 2. The proximal mount assembly 200 is configured in any appropriate manner to be pivotally connected to the frame 110 of the prosthetic knee 100 at the pivot location 120. For example, the proximal mount assembly can be configured to have bores that receive pivot rods so that the proximal mount assembly 200 may pivot with respect to the frame 110.

The specific details of the pivot structure 120 may be those known in the art, for example pivot structures available as part numbers FRM61721U, MAK01501, MAK01502, FRM61524, MAK01503, FRM31522, and FRM61523, all available from Össur hf., Reykjavik, Iceland. One requirement of any pivot structure is that the proximal mount assembly 200 should be able to pivot with respect to the frame 110. Of course, other configurations will be apparent to those of ordinary skill in the art of prosthetic knees.

The proximal mount assembly 200 may also be configured to receive a conventional pyramid coupling connection 250, as discussed above. However, any suitable conventional coupling mechanism, such as clamps or threaded mounts may be used.

The proximal mount assembly 200 may include a filler 210 or guard that is used to protect the proximal mount assembly 200 and the frame 110. The filler 210 may also protect the clothing of a user from becoming damaged. The filler 210 can be made of any appropriate material, including hard and soft plastics, and is an optional component of the prosthetic knee 100.

The proximal mount assembly 200 may also include a plurality of flange portions 240 located at a posterior portion 242 of the proximal mount assembly 200. The flanges can define a cut-out or recessed portion 230. Each flange portion 240 can also include a bore 220 therethrough.

Figure 4:
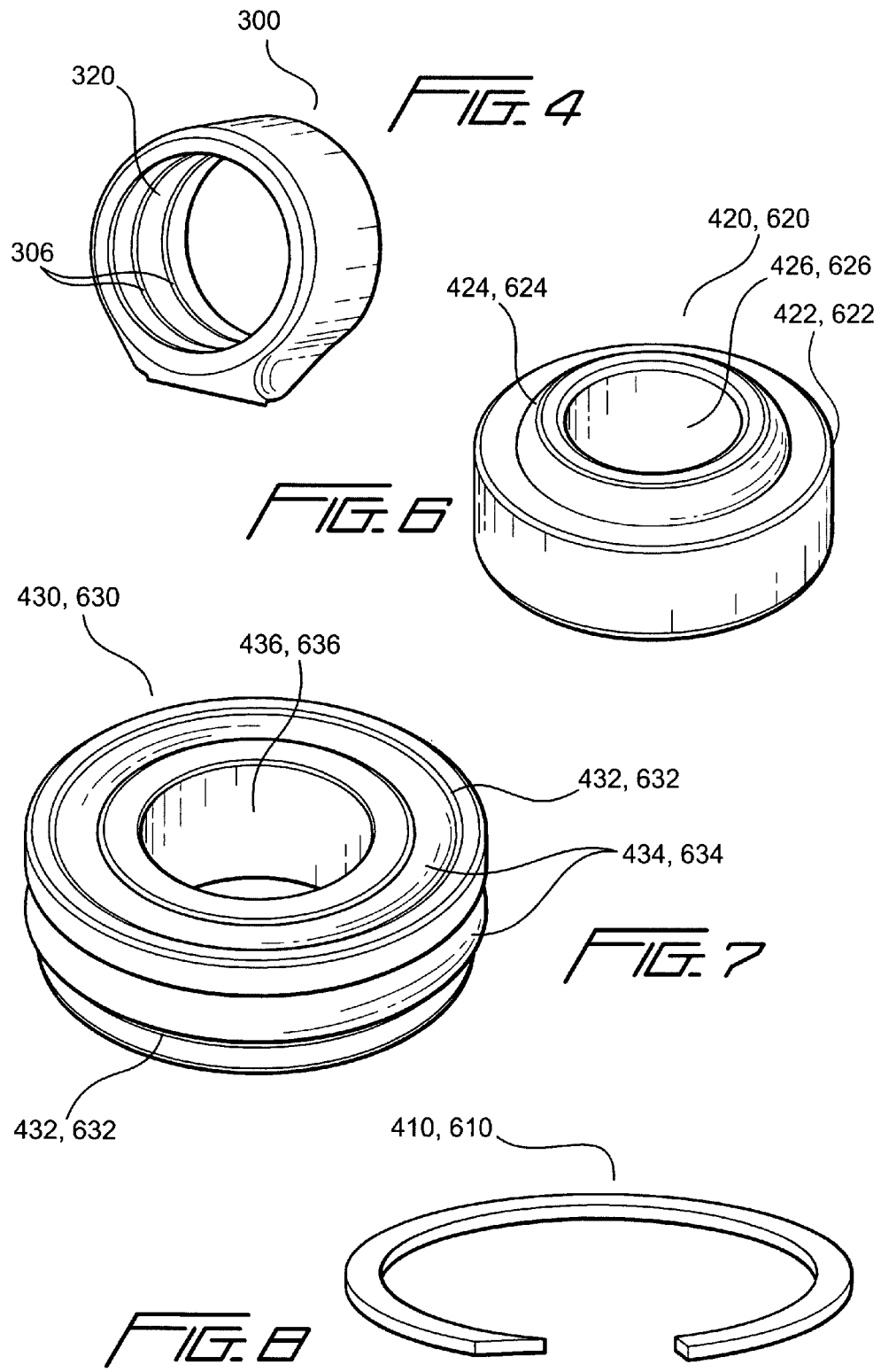
FIG. 4 is a perspective view of the second mount or proximal connection assembly shown in FIG. 1.

The bores 220 in the flanges 240 are configured to receive a cylindrical rod 310 that forms the basis for a proximal connection assembly 300, as seen in FIG. 4. The proximal connection assembly 300 consists of a member having a bore 320 for receiving the components of a proximal bearing assembly 400.

The proximal connection assembly 300 may also include an extending portion 302, as shown in FIG. 2, that can be used to connect to a linkage or a control unit 500 in any conventional manner, such as a bore 304 in the extending portion that receives a connecting pin 350. The specific structure of how the proximal connection assembly 300 is connected to a linkage or control unit 500 may be any connection known to one of ordinary skill in the art, such as threaded connections, press-fitting or welding.

In an alternative construction, the proximal connection assembly 300 may not have the extending portion 302, but instead may be connected directly to the linkage or control unit 500. Such a connection may be accomplished in any suitable manner known to those having ordinary skill in the art of orthotic and prosthetic devices.

Figure 5:
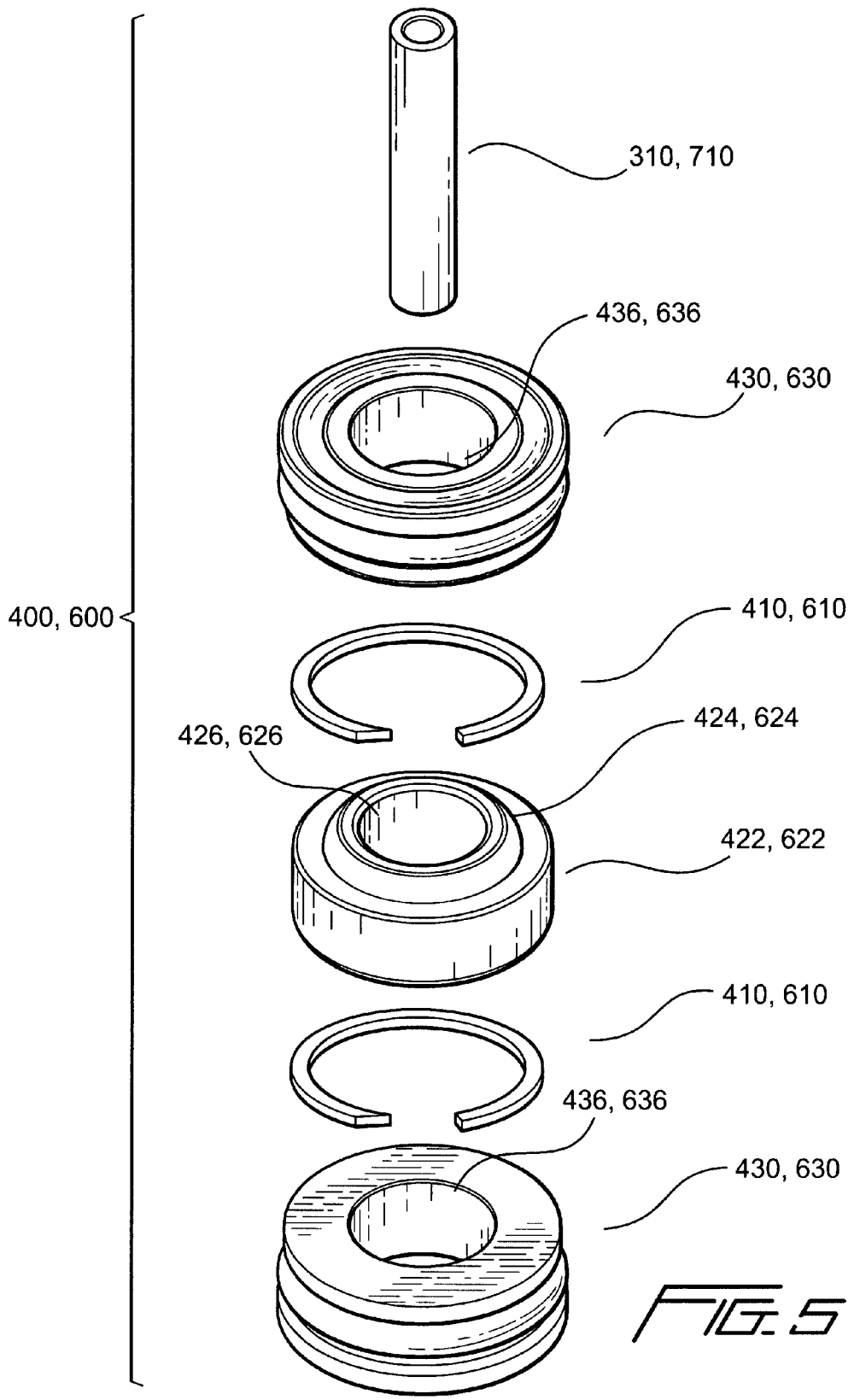
FIG. 5 is an exploded perspective view of the components of the bearing assemblies shown in FIG. 1.

The proximal connection assembly 300 is configured to receive the proximal bearing assembly 400. The proximal bearing assembly 400, seen in FIG. 5 in an exploded view, consists of a number of components that are received within the bore 320 of the proximal connection assembly 300.

The proximal bearing assembly 400 includes a bearing portion 420 that is composed of a swivel portion 424 that is received within an engaging ring 422, as can be seen in FIG. 6. The swivel portion 424 is able to swivel within the engaging ring 422 in multiple axes. The swivel portion 424 includes a bore 426 for receiving the cylindrical rod 310 therein.

The cylindrical rod 310 may be received within the bore 426 in a near press-fit manner, or simply in a machine-fit manner. Due to variations in machining tolerances, the cylindrical rod 310 may easily slide within the bore 426, or the cylindrical rod 310 may engage the bore 426 in a frictional manner.

The engaging ring 422 is received within the bore 320 of the proximal connection assembly 300, as can best be seen in FIG. 2. The engaging ring 422 may be machined to fit within the bore 320 with a machine-fit, and may also be adhesively retained within the bore 320 using any known appropriate conventional adhesive.

The bore 320 may include grooves or receiving portions 306 that are positioned to be located on either side of the engaging ring 422. The receiving portions 306 are configured to receive retaining rings 410, shown in FIG. 8, which are placed on either side of the engaging ring 422 to maintain the engaging ring 422 within the bore 320, as can be seen in FIG. 2.

The proximal bearing assembly 400 may also include a plurality of seals 430. Each seal includes receiving portions 432 configured to receive sealing members 434. One sealing member 434 may be located around the circumference of the seal 430, as shown in FIG. 7, in order to provide an air and fluid tight seal between the seal 430 and the bore 320 as can be seen in FIG. 2. Another sealing member 434 can be provided around a side of the seal 430, as shown in FIG. 7, in order to provide an air and fluid tight seal between the seal 430 and the flange 240 as can be seen in FIG. 2. The seal members 434 may be conventional O-rings or gaskets, or any other suitable sealing structure.

One of each of the seals 430 can be provided on either side of the engaging ring 422 and in contact with the swivel portion, as shown in FIG. 2. The space between the engaging ring 422 and either seal 430 may be packed with grease, or any other suitable lubricant. In this manner, the swivel portion 424 is provided with lubrication between the swivel portion 424 and the engaging ring 422. Thus, the swivel portion 424 may freely swivel within the engaging ring 422 in order to prevent torsional loads from being transmitted through to the proximal connection assembly 300.

The seals 430 also have bores 436 that may be configured to be press-fit onto the cylindrical rod 310, or alternatively the bores 436 could have a clearance-fit, or a machine-fit. Even if the bores 436 have only a clearance-fit, the grease or lubricant that is packed within the space between the seals 430 and the engaging ring 422 is retained due to the sealing member 430 on the side of the seals 430 that engages the flanges 240.

As shown in FIG. 2, the cylindrical rod 310 engages the flanges 240, the seals 430, and the swivel portion 424 of the bearing assembly 400. The cylindrical rod 310 is press fit at both ends into either of the bores 220 of the flange portions 240. With this configuration, the proximal connection assembly 300 can rotate freely about the cylindrical rod 310 in all three axes for at least a predetermined amount of rotation. Thus, the proximal connection assembly 300 transmits only an axial load to the linkage or control unit 500. This allows any linkage or control unit to have a reduced size, since they are not required to be capable of withstanding torsional forces. In addition, there is reduced risk of binding for a control unit.

Figure 3:
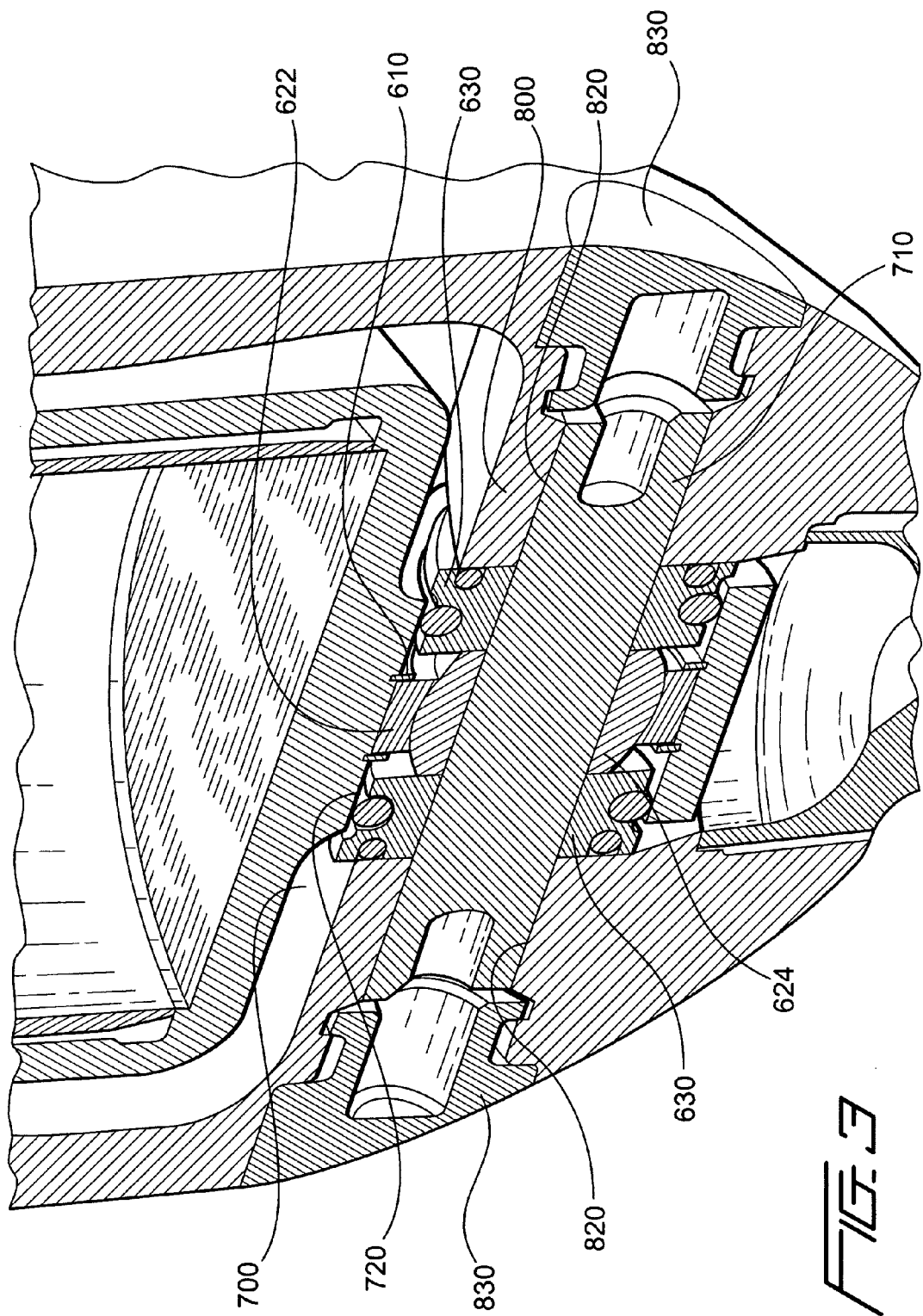
FIG. 3 is a close up sectional view of the distal bearing assembly shown in FIG. 1.

In the exemplary embodiment, shown in FIGS. 1-3, the prosthetic knee 100 includes a control unit 500. A control unit that is active or passive, as is well known in the art of prosthetic knees, may be provided. Exemplary control units may be used such as control units having the part numbers SNJ01800U, and SNJ01800LU, both available from Össur hf., Reykjavik, Iceland. However, a control unit is not necessary, and instead a simple mechanical linkage could be provided. In either case, the proximal end 520 may include a linkage or piston rod 510 and the distal end 530 may define the distal connection assembly 700.

The distal connection assembly 700, which can best be seen in FIG. 3, is of a similar design as the proximal connection assembly and includes a cylindrical rod 710 and a bore 720 therethrough. The distal connection assembly can include grooves or receiving portions similar to grooves or receiving portions 306 for receiving retaining rings 610, which are identical to retaining rings 410.

In the embodiment shown in FIGS. 1-3 the distal connection assembly is shown as being integral with the control unit 500. Of course, many alternative constructions will be readily apparent to those having ordinary skill in the art of orthotic and prosthetic devices.

The bore 720 of the distal connection assembly 700 is configured to receive a distal bearing assembly 600 that is identical in construction to the proximal bearing assembly 400. The distal bearing assembly 600 includes a bearing portion 620 that includes an engaging ring 622 and a swivel portion 624 having a bore 626 therethrough and such that the swivel portion 624 and the engaging ring 622 are configured to engage each other in a swivel fashion, as previously described.

The distal bearing assembly 600 also includes a plurality of seals 630 having bores 636 therethrough and receiving portions 632 for receiving sealing members 634 in an identical manner to the seals 430 discussed above.

The distal mounting assembly 800 shown in FIG. 3 consists of bores 820 passing through a distal portion of the frame 110 of the prosthetic knee 100. The cylindrical rod 710 can be press-fit into the bores 820 of the frame 110, in a manner similar to that discussed above with respect to the cylindrical rod 310 of the proximal connection assembly 300. In the exemplary embodiment shown in FIG. 3, there are protective plugs 830 received within the bores 820 of the frame 110. These plugs are not a necessary component, but can serve as an aesthetic component and to keep dirt and debris from accumulating within the bores 820.

The distal bearing assembly 600 and the distal connection assembly 700 function in exactly the same manner as discussed above with respect to the proximal bearing assembly 400 and the proximal connection assembly 300. That is, torsional forces are not transmitted through the distal connection assembly 700 to the linkage or control unit 500, due to the swivel function of the distal bearing assembly 600.

In use, the prosthetic knee 100 functions in a manner known to those having ordinary skill in the art of prosthetic knees. The frame 110 and the proximal mount assembly 200 rotate with respect to each other to simulate the motion and function of the human knee joint. During everyday use of a prosthetic knee, the prosthetic knee will be subject to both axial and torsional loading. The momentum free bearings described herein allow certain components of the prosthetic knee to be isolated from torsional loading.

In this manner, with both a proximal momentum free bearing assembly and a distal momentum free bearing assembly, a linkage or control unit is subject only to an axial loading along its length. As previously discussed, the size of a linkage or control unit may be reduced, and the overall weight of the prosthetic limb may be reduced, as a result of the use of a proximal momentum free bearing assembly and a distal momentum free bearing assembly.

Additionally, if any type of hydraulic control unit is used, there is a reduced possibility of binding between the piston and cylinder of the control unit, since neither the piston nor the control unit see a torsional load. Thus, the load is transmitted axially through and within the piston head and cylinder, in the manner that hydraulic cylinders are designed. This also applies to pneumatic pistons and cylinders as well as any other known type of control unit.

C. Alternate Embodiments

While the momentum free bearings are shown in use in a prosthetic knee having a control unit, many alternative uses and embodiments will be readily apparent to those having ordinary skill in the art of orthotic and prosthetic devices.

For example, the momentum free bearings can be utilized without the seals described, or with alternatively constructed seals. Such alternative seals could include replacing the structure of the seals described herein with a gasket material, or with a seal having only seal members along one surface.

In other alternatives, the momentum free bearings can be used in orthotic devices such as braces for the knee or elbow. Also, the momentum free bearings may be used in orthotic devices designed to support any part of the body.

Further, the momentum free bearings may be used in any prosthetic device such as prosthetic elbow, hip or ankle joints. The momentum free bearings can be used in any type of prosthetic device where it is desired to isolate components of the prosthetic limb from torsional loading.

The components of the momentum free bearings can be constructed from any suitable materials, for example any suitable lightweight structural materials such as stainless steels, aluminums, plastics, or any suitable combinations thereof. The components of the prosthetic knee can be made from any suitable known materials, such as stainless steel, aluminum, plastic, carbon fiber or glass fiber composites or any suitable combinations thereof.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments and method steps. In addition to the variations described herein, other known equivalents for each feature can be mixed and matched by one of ordinary skill in this art to construct a momentum free bearing for use in prosthetic limbs in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims below.

The invention claimed is:

1. An orthotic or prosthetic joint comprising:
a frame having proximal and distal portions;

a first proximal mount pivotally engaging the frame; and a linkage having proximal and distal portions, and a first pivotal connection to the first proximal mount at the proximal portion thereof, and the linkage having a second pivotal connection to a distal portion of the frame at the distal portion thereof such that the linkage is free from torsional loading and rotates with three degrees-of-freedom with respect to the frame;

wherein the first and second pivotal connections of the linkage each include a bearing assembly having:
an engaging ring;
a swivel portion defining a bore and received within the engaging ring so as to freely rotate in at least three directions; and
a cylindrical rod engaging the bore within the swivel portion;

wherein the engaging ring of the first pivotal connection engages the linkage proximal portion and the engaging ring of the second pivotal connection engages the linkage distal portion; and wherein first and second ends of the cylindrical rod of the first pivotal connection engage the first proximal mount in a fixed manner, and first and second ends of the cylindrical rod of the second pivotal connection engage the distal portion of the frame.

2. The orthotic or prosthetic joint according to claim 1, wherein the bearing assembly of the first pivotal connection further has a second mount at the linkage proximal end defining a bore and receiving the engaging ring therein.

3. The orthotic or prosthetic joint according to claim 2, wherein the bearing assembly of the first pivotal connection further has:
a plurality of retainer rings positioned within the second mount bore on either side of the engaging ring and retaining the engaging ring within the second mount bore.

4. The orthotic or prosthetic joint according to claim 3, further comprising:
a plurality of seals positioned within the second mount bore on either side of the retainer rings.

5. The orthotic or prosthetic joint according to claim 2, wherein the second mount further has an extending portion that is mounted to the linkage proximal portion.

6. The orthotic or prosthetic joint according to claim 5, wherein the linkage releasably engages the extending portion.

7. The orthotic or prosthetic joint according to claim 1, further comprising a plurality of seals each seal having at least one receiving portion and at least one sealing member received therein.

8. The orthotic or prosthetic joint according to claim 7, wherein the at least one sealing member is resilient so as to retain its shape when in an unstressed condition.

9. The orthotic or prosthetic joint according to claim 1, wherein the linkage is an active or passive control unit.

10. The orthotic or prosthetic joint according to claim 1, wherein the first proximal mount further has a plurality of flange portions defining bores therethrough;
wherein the cylindrical rod of the bearing assembly of the first pivotal connection is fixedly received within the plurality of bores such that the linkage is free to rotate in three directions with respect to the first proximal mount.

11. The orthotic or prosthetic joint according to claim 1, wherein the frame further has a plurality of bores formed within a distal portion thereof;
wherein the cylindrical rod of the bearing assembly of the second pivotal connection is received within the plurality of bores such that the linkage is free to rotate in three directions with respect to the frame.

12. The orthotic or prosthetic joint according to claim 1, wherein the first proximal mount and the distal portion of the frame each define a plurality of bores therethrough for fixedly receiving the cylindrical rods of a bearing assembly of the first and second pivotal connections respectively, such that the linkage is free to rotate in three directions with respect to both the first proximal mount and the frame, respectively.

\* \* \* \* \*